(12) United States Patent
Rolnick et al.

(10) Patent No.: US 6,971,995 B2
(45) Date of Patent: Dec. 6, 2005

(54) METHOD FOR SPLINTING RIB INJURIES

(76) Inventors: Michael Alan Rolnick, 12533 Folly Quarter Rd., Ellicott City, MD (US) 21042; Matthew Perry Warden, 386 Commercial St. Apt 4C, Boston, MA (US) 02109; Robert Allen Van Wyk, 10801 Starkey Rd., #104-16, Largo, FL (US) 33777

( * ) Notice: Subject to any disclaimer, the term of this patent is extended or adjusted under 35 U.S.C. 154(b) by 12 days.

(21) Appl. No.: 10/764,794

(22) Filed: Jan. 26, 2004

(65) Prior Publication Data

US 2005/0033209 A1   Feb. 10, 2005

Related U.S. Application Data

(60) Provisional application No. 60/442,601, filed on Jan. 27, 2003.

(51) Int. Cl.$^7$ ................................. A61F 5/00
(52) U.S. Cl. .......................... 602/12; 602/5
(58) Field of Search .............. 602/12, 72, 71, 602/5, 19, 20, 60; 128/102.1; D24/190

(56) References Cited

U.S. PATENT DOCUMENTS

| | | | | |
|---|---|---|---|---|
| 2,541,487 A | * | 2/1951 | Triplett | 602/19 |
| 2,923,664 A | * | 2/1960 | Cook et al. | 206/210 |
| 3,400,710 A | * | 9/1968 | Goldstein | 602/19 |
| 3,561,436 A | * | 2/1971 | Gaylord et al. | 602/19 |
| 4,680,205 A | * | 7/1987 | Lerner et al. | 428/29 |

* cited by examiner

*Primary Examiner*—Henry Bennett
*Assistant Examiner*—Shumaya B. Ali
(74) *Attorney, Agent, or Firm*—Chalin A. Smith; Smith Patent Consulting

(57) ABSTRACT

A method for splinting rib injuries is disclosed. A pair of anchor strips having a plurality of fasteners on their exposed surfaces are attached to the skin of the chest cavity by an adhesive, the strips being more or less vertically oriented and equidistantly spaced from the injury. Elastomeric straps having a plurality of fastener receivers are removably fastened to the anchor strips across the injury so as to produce a stabilizing/reducing force at the injury. Tension in the straps and orientation of the straps are adjusted to maximize patient comfort. In another embodiment a pad is placed between the elastomeric straps and the chest wall. In other embodiments the pad is a hot or cold compress. In yet another embodiment the pad is connected to a cold therapy machine.

13 Claims, 9 Drawing Sheets

A-A
SCALE 2:1

METHOD FOR SPLINTING RIB INJURIES

This application claims the benefit of provisional application 60/442,601 filed Jan. 27, 2003.

BACKGROUND OF THE INVENTION

The present invention relates to stabilizing/splinting fractures of bones, bone contusions, and sprains. More specifically it relates to the splinting of rib injuries.

Patients with blunt chest trauma are frequently seen in hospital emergency departments. Major initial concerns for the treating physician are lung collapse, which is ruled out by a chest x-ray, and other injuries that can be ruled out with a combination of physical exam and possibly other imaging studies. Once the evaluation is completed, the majority of patients are discharged home with narcotic pain medications and an incentive spirometer, a device used by the patient to monitor the volume of air inhalation during breathing. An incentive spirometer is imperative for chest wall injuries because it helps to facilitate maximal lung expansion, thereby minimizing the chance of minor lung collapse and subsequent pneumonia. With the exception of pain medication, no treatment is given to patients with rib injuries.

Splints and braces for stabilization of bony injuries and ligamentous injury are well known in the art and are used on all bony injuries except for rib injuries. Rib injuries present a unique splinting challenge due to their location. Proper splinting technique teaches that a splint should extend to include the joint on either side of the injury. Attempts have been made to follow this technique by splinting rib injuries using a brace which wraps circumferentially around the body. However, this proves unsatisfactory because the brace significantly limits lung expansion (both lungs), is associated with high rates of post-injury pneumonia, and is uncomfortable for the patient.

Applying an inelastic adherent patch over the site of a rib injury may give temporary relief. However, it is suboptimal because the amount of reducing force applied to the fracture will be dependant on the amount of chest expansion since the adherent patch is essentially inelastic. Additionally, it is not possible to adjust the patch to optimize patient comfort after application. Showering is problematic as the adherent patch must be removed and reapplied after showering, a task beyond the skill of most patients.

It is, accordingly, an object of this invention to produce a method for splinting rib injuries which affects only the injured portion of the chest allowing unimpeded expansion of the uninjured portion of the chest.

It also an object of this invention to produce a method for splinting rib injuries which produces a reducing force at the injury site even during minimal chest expansion.

It is further an object of this invention to produce a method for splinting rib injuries which allows adjustment after application of the splinting device so as to maximize patient comfort.

It is further an object of this invention to produce a method for splinting rib injuries in which the reducing force can be temporarily removed so as to allow the patient to fully expand the chest during, for instance, use of a incentive spirometer, without complete removal of the splinting means.

It is additionally an object of this invention to produce a method for splinting rib injuries having means which can be removed, reapplied and adjusted by the patient for maximum comfort, for instance, for showering.

It is also an object of this invention to produce a method for splinting rib injuries which is low cost.

SUMMARY OF THE INVENTION

These and other objects are accomplished by the invention herein disclosed which is a method for splinting rib injuries that includes placing two anchor strips on the chest wall approximately equidistant from the rib injury in a more or less vertical orientation, and placing elastomeric straps across the injury in a more or less horizontal manner so as to produce a stabilizing force on the injury site, the elastomeric straps being removably affixed to the anchor strips by hook and loop fasteners. An initial tension is supplied to the elastomeric straps during placement. In this manner a reducing force is produced across the injury site regardless of the degree of chest expansion, the reducing force increasing with increasing expansion of the chest. The rate of increase in the reducing force as a function of degree of chest expansion is determined by the spring-constant of the elastomeric strap. Elastomeric straps having a low spring-constant will provide less increase in the reducing force with increased chest expansion than elastomeric straps having a higher spring-constant. By choosing the proper combination of elastomeric strap spring-constant, and initial tension in the strap, a reducing force profile may be created which provides maximum patient comfort. Elastomeric straps with spring constants from very low (for instance, for pediatric applications) to extremely high are anticipated.

The elastomeric straps may be removed and reapplied, their placement and the amount of initial tension being adjusted after so as to maximize patient comfort. Tension in the elastomeric straps may be removed by the patient by unfastening one end from its anchor strip so that the patient can take deep breaths and use a spirometer per the physicians instructions. With minimal training, the patient can completely remove the splint including the anchor strips and reapply the splint with new anchor strips, for instance, after showering.

Other embodiments use other fastening methods for removably affixing the elastomeric straps to the anchor strips. For instance, hooks which engage the fabric of the elastomeric strap rather than pile affixed to the strap, may be mounted to the anchor strips. Or such hooks may engage a plurality of eyelets in the fabric of the elastomeric strap. Alternatively, buttons or snaps may be used.

In another embodiment a pad is placed between the elastomeric straps and the chest wall. In other embodiments this pad is a hot or cold compress. In yet another embodiment the pad is attached to a cold therapy machine.

The disclosed rib splinting method provides stabilization to the side of the rib cage having the injured ribs only. Expansion of the uninjured side is not impeded by the device. The splint provides a stabilizing force to the injury site even during minimal chest expansion, and may be adjusted after application to maximize patient comfort. The patient can release the elastomeric strips so as to be able to take deep breaths as required and reattach them afterwards. The entire splint can be removed and reapplied by the patient for showering. The manufacturing costs of the rib splint are low due to its simple construction and the common materials used.

The more important features of the invention have been outlined rather broadly in order that the detailed description thereof that follows may be better understood, and in order that the present contribution to the art may be better appreciated. There are, of course, additional features of the

DESCRIPTION OF THE EMBODIMENTS

As used herein, medial is defined as the direction toward the center of the body of a patient, and lateral is defined as the direction away from the center of the body.

Figure 1:
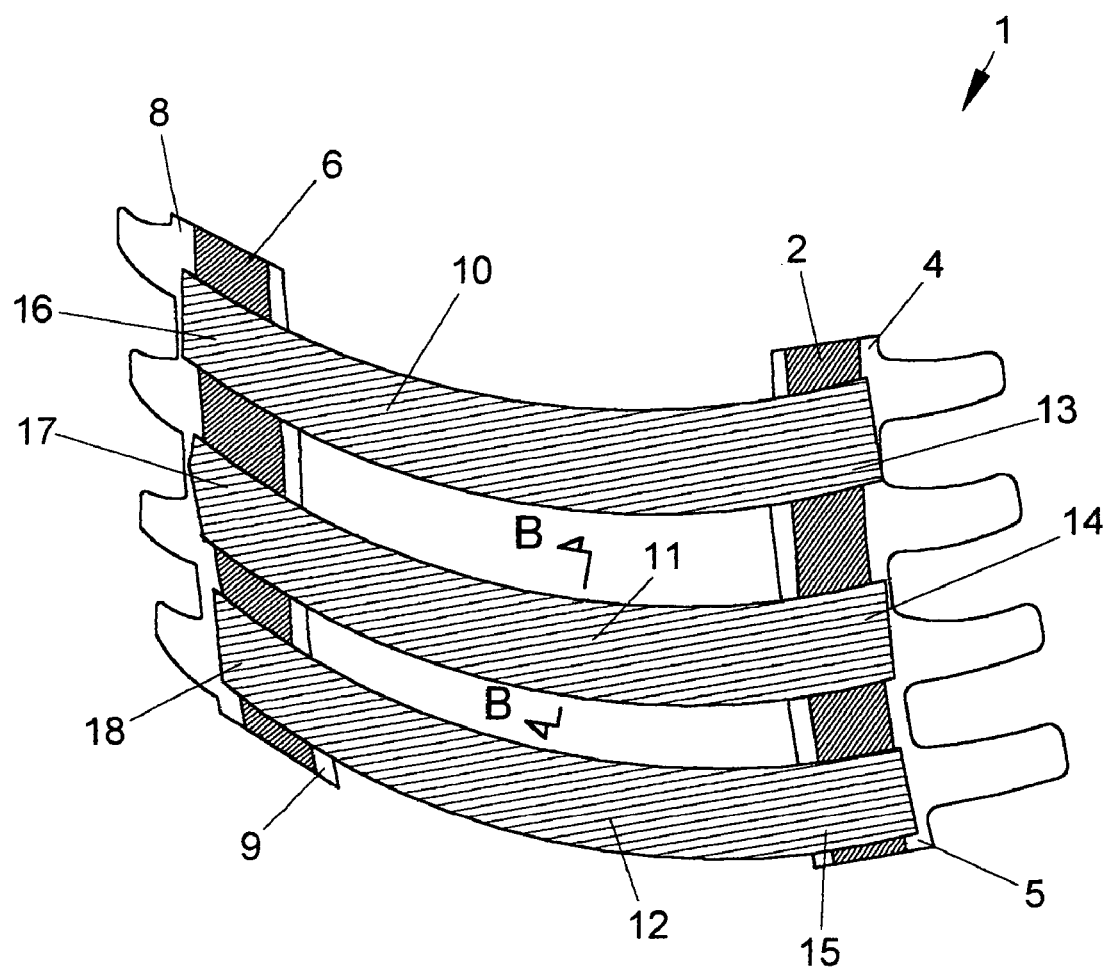
FIG. 1 is a perspective view of a rib splint constructed in accordance with the principles of this invention.

Referring to the Figures, as best seen in FIG. 1, Rib Splint 1 comprises a more or less vertical, medial anchor strip 2 having an upper end 4 and a lower end 5 and a lateral anchor strip 6 having an upper end 8 and a lower end 9. Splint 1 also comprises a plurality of more or less horizontal elastomeric straps 10, 11, and 12 having medial ends 13, 14 and 15 respectively and lateral ends 16, 17 and 18 respectively, the medial ends being removably attached to medial anchor strip 2, and the lateral ends being removably attached to lateral anchor strip 6. Three elastomeric straps are shown, however, the actual number used will depend on the injury being treated and may be more or less.

Figure 2:
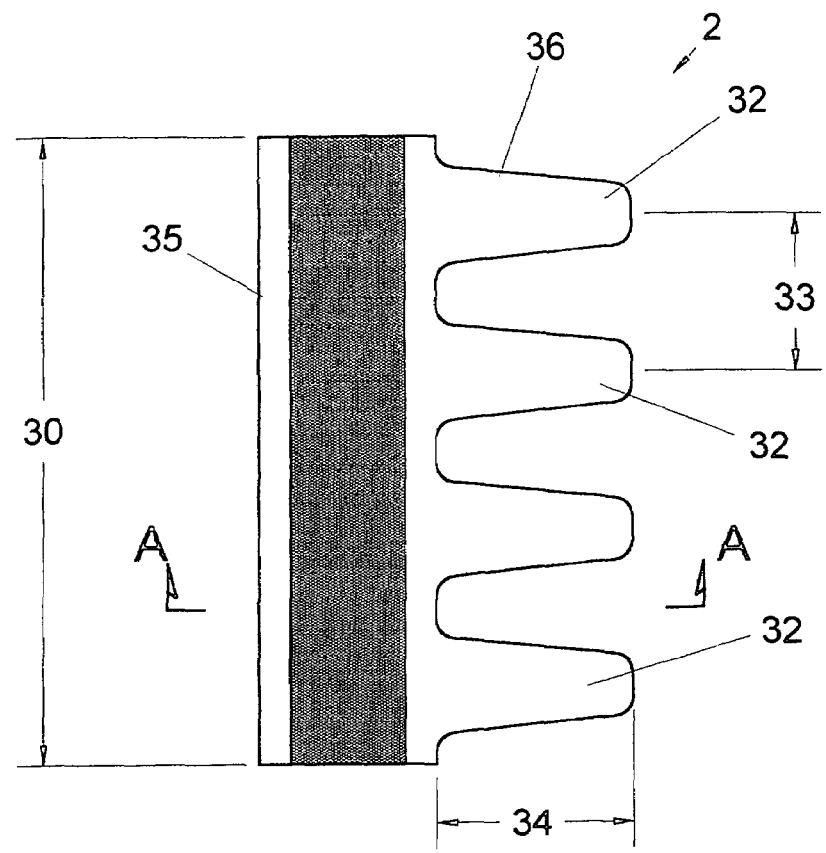
FIG. 2 is a plan view of the medial anchor strip of the object of FIG. 1.
Figure 3:
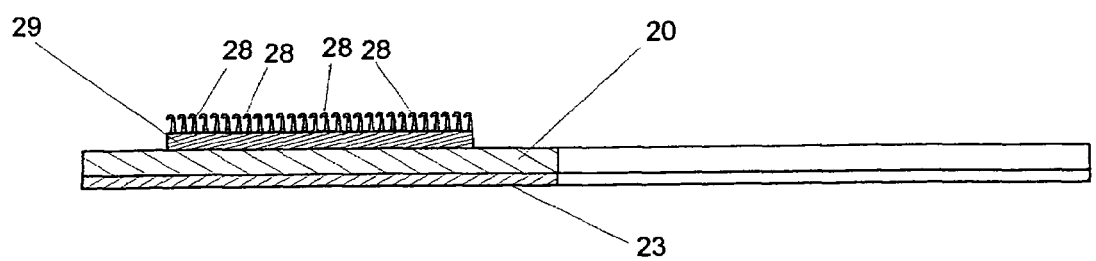
FIG. 3 is an expanded sectional view of the object of FIG. 2 along direction A—A.

Referring to FIGS. 2 and 3, medial anchor strip 2 of length 30 has a lateral edge 35 and a medial edge 36 which forms a plurality of medially extending, elongated portions 32 of length 34 spaced distance 33 apart. Elongated portions 32, when strip 2 is applied to a chest wall, wrap partially around the curvature of the wall medially so as to give increased holding power when the strip is subjected to a lateral force, as during use. Length 30 is approximately an integral multiple of distance 33. As best seen in FIG. 3, anchor strip 2 has a first layer 20, formed of a compliant material such as polymeric foam, a second layer 23 formed of an adhesive material suitable for application to the skin in medical applications, and a third layer 29 having a first surface which is permanently joined to layer 20 and a second surface having a plurality of hook-shaped protrusions 28 forming fasteners suitable for removably fastening to a suitable pile fabric. Lateral anchor strip 6 is identical in construction to medial anchor strip 2.

Figure 4:
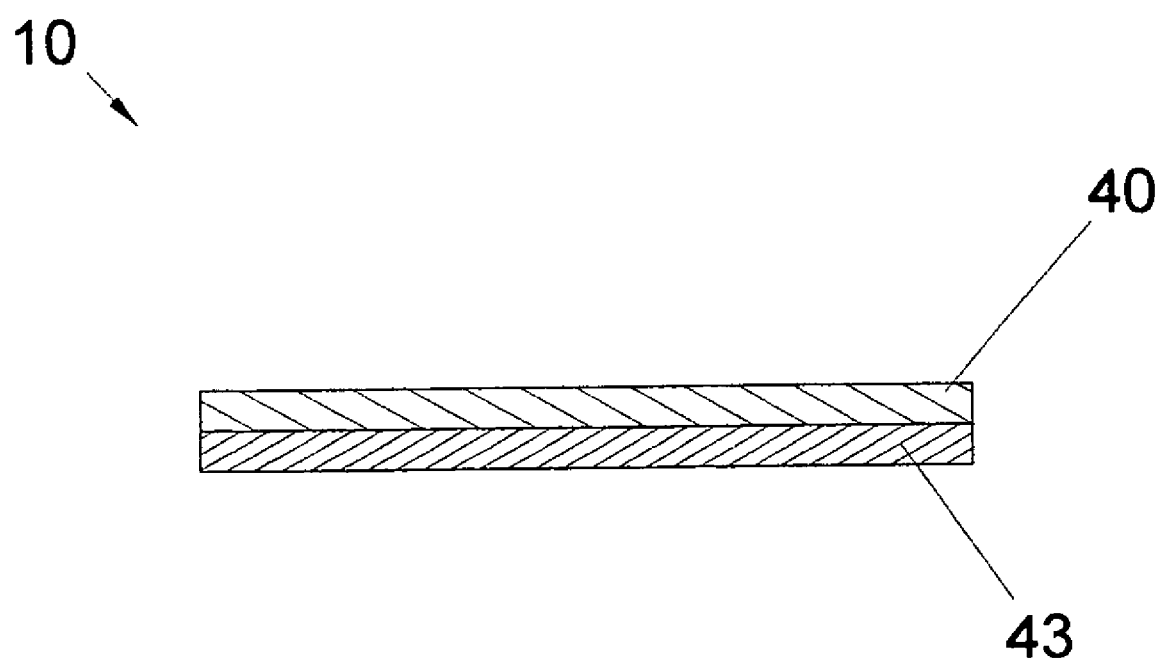
FIG. 4 is an expanded sectional view of an elastomeric strap of the object of FIG. 1 along direction B—B.

Referring to FIG. 4, elastomeric strap 10 comprises a layer 40 formed of a suitable elastomeric material and a layer 43 forming fastener receivers formed from a pile material suitable for removably fastening to the hook-shaped protrusions 28 of layer 29 of medial anchor strip 2. Layer 43 may extend the entire length of the strap or may only cover areas adjacent to the ends of the strap.

Figure 5:
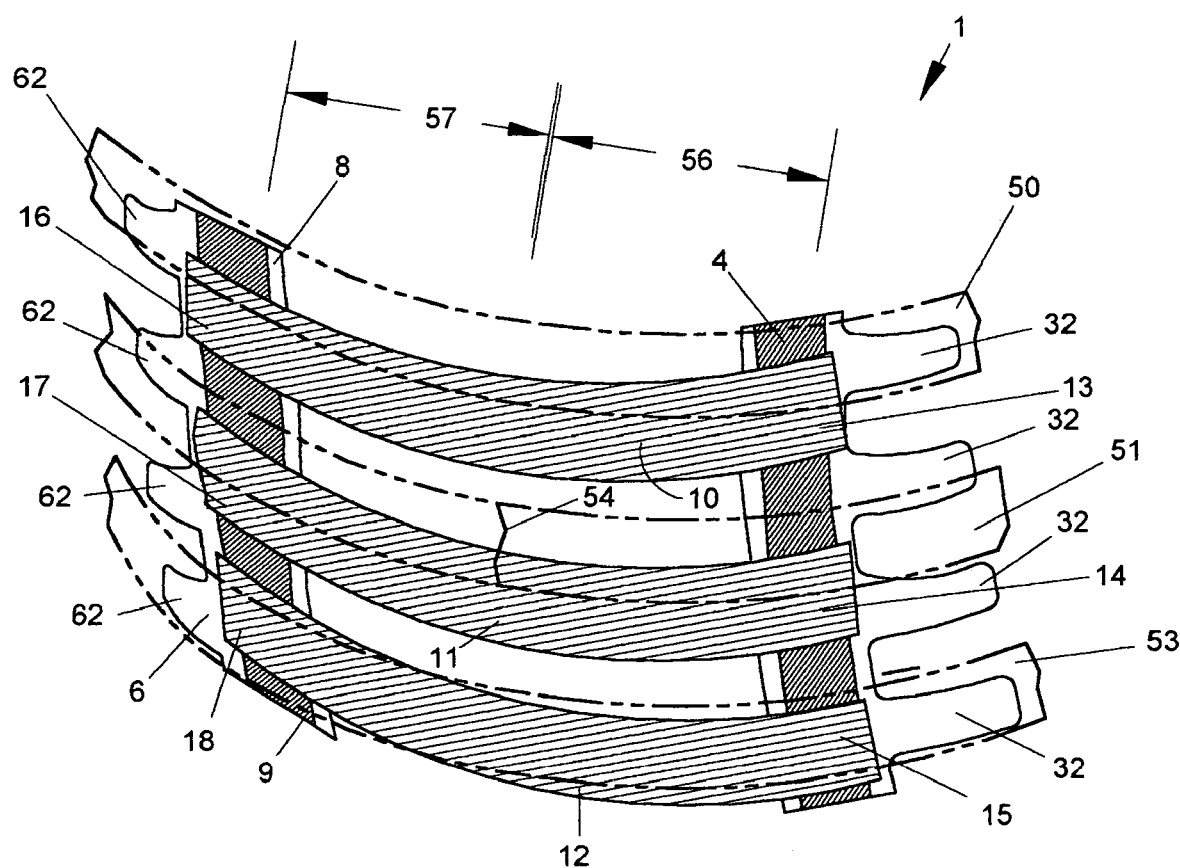
FIG. 5 is a perspective view of the object of FIG. 1 showing the positional relationship of the device to a rib fracture during use.

Referring to FIG. 5, rib 51 has fracture 54, while ribs 50 and 53 are not fractured. Rib splint 1 is applied in the following manner: the location of the fracture is determined by x-ray and/or physical examination. Anchor strip 2 is applied to the chest wall more or less vertically at a distance 56 medial to the fracture, distance 56 being determined by the attending physician, elongated portions 32 wrapping partially around the chest wall. Anchor strip 6 is applied more or less vertically a distance 57 lateral to the fracture, distance 57 being approximately equal to distance 56, elongated portions 62 wrapping partially around the chest wall. Medial end 14 of elastomeric strap 11 is removably affixed to anchor strip 2 near its midpoint. Elastomeric strap 11 is stretched so as to apply an initial reducing force to the injury, and lateral end 17 is removably affixed to anchor strip 6 near the midpoint of the anchor strip. In the same manner, medial end 13 of elastomeric strap 10 is removably affixed to upper end 4 of anchor strip 2, stretched to provide an initial reducing force and lateral end 16 removably affixed to upper end 8 of lateral anchor strip 6. Medial end 15 of elastomeric strap 12 is removably affixed to lower end 5 of medial anchor strip 2, stretched to provide an initial reducing force and lateral end 18 removably affixed to lower end 9 of anchor strip 6.

Figure 6:
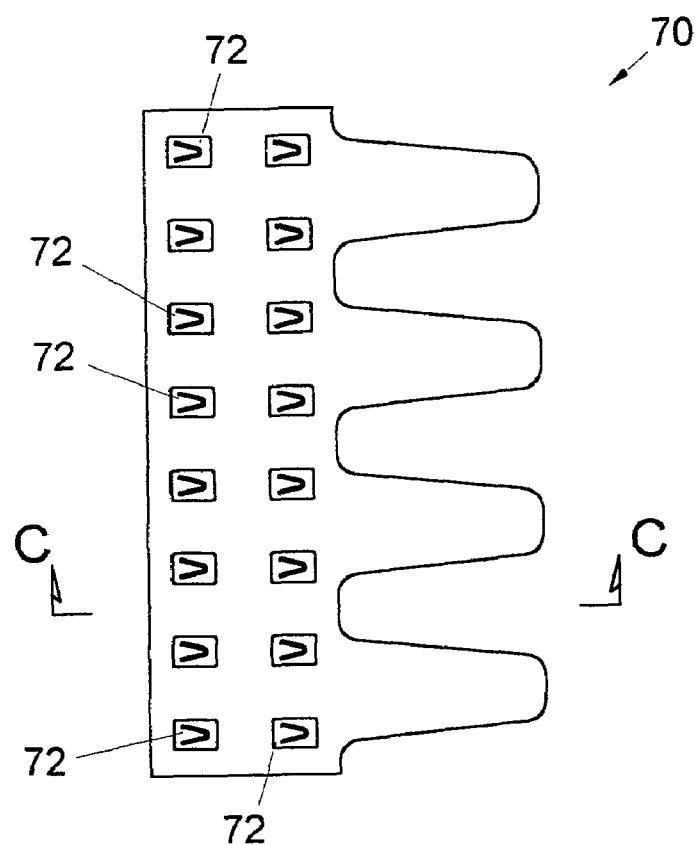
FIG. 6 is a plan view of an anchor strip having alternate fasteners.
Figure 7:
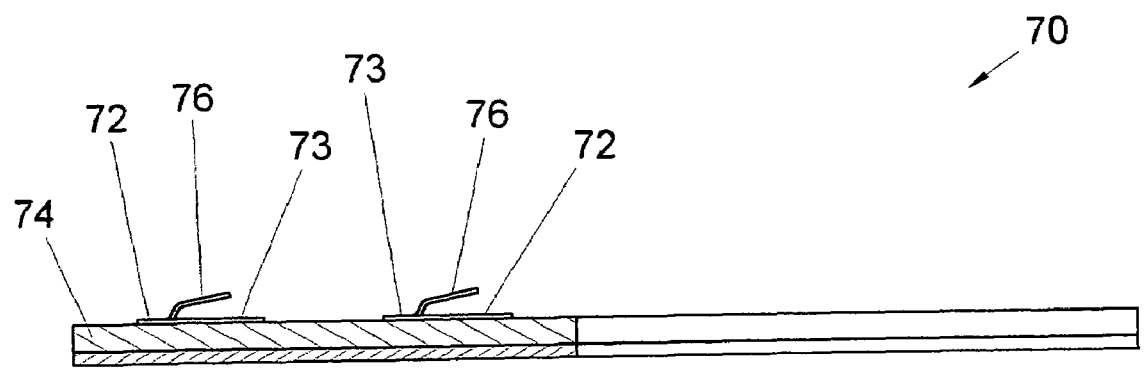
FIG. 7 is an expanded sectional view of the object of FIG. 6 along direction C—C.

A medial anchor strip with alternative fasteners is shown in FIGS. 6 and 7. Medial anchor strip 70 is designed for use wit elastomeric straps which do not have a pile fabric layer attached. It is identical in configuration and function to anchor strip 2 except tat third layer 29 of strip 2 (FIG. 3) with its multiple hooked protrusions, is replaced by a plurality of components 72 having a base 73 attached to second layer 74, and a hook portion 76. Hook portion 76 engages the fabric of an elastomeric strap, or alternatively, eyelets in the elastomeric strap (not shown).

Additional embodiments of the medial anchor strip with alternative fasteners are shown in FIGS. 8 and 9.

Figure 8A:
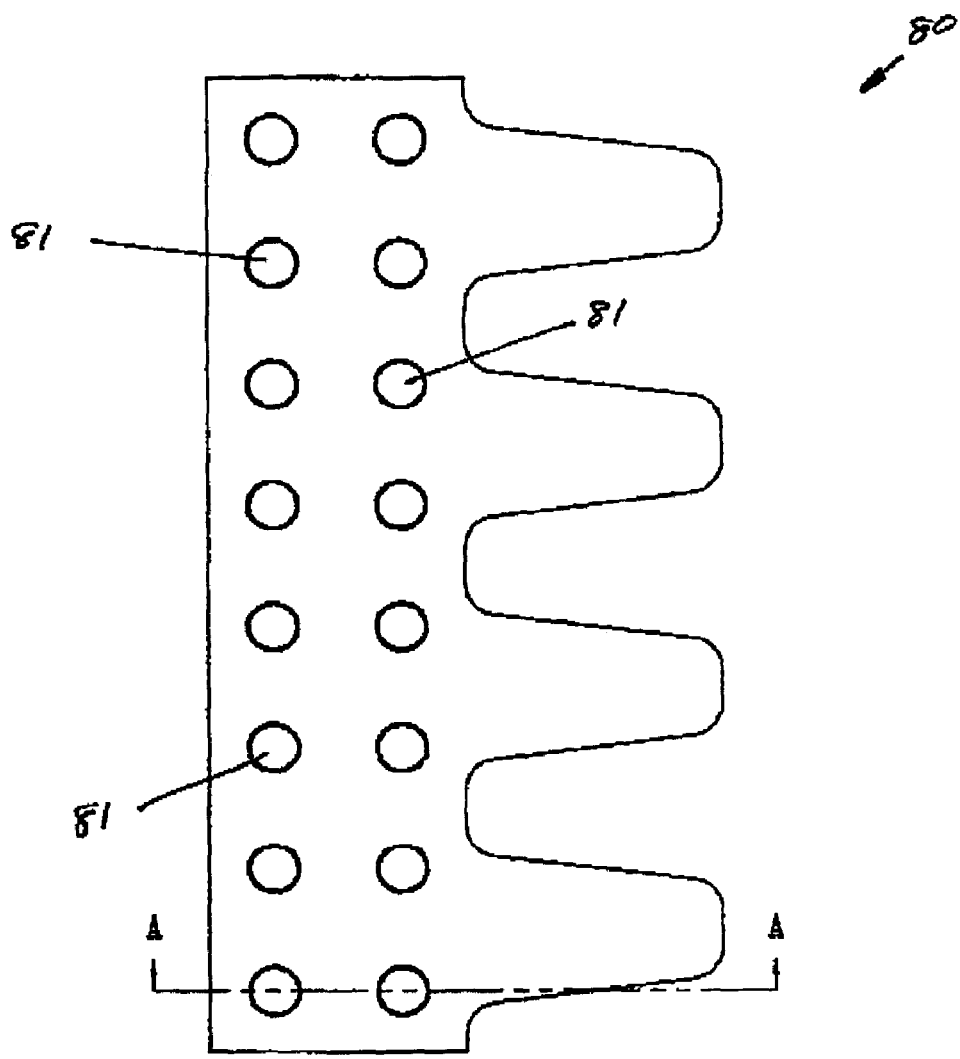
FIG. 8A is a plan view of an anchor strip having alternate fasteners (i.e., buttons).
Figure 8B:
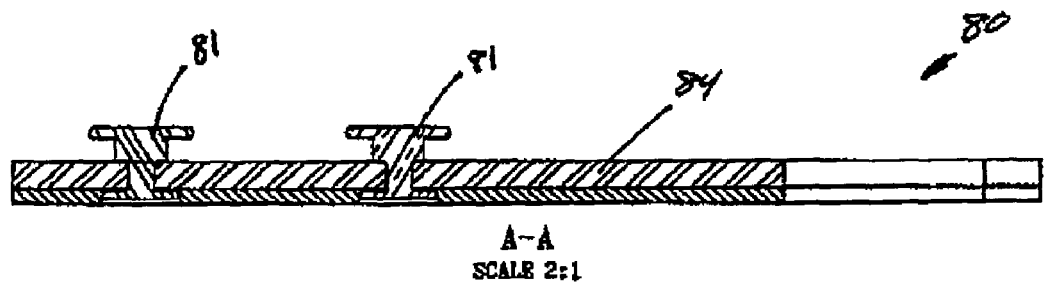
FIG. 8B is an expanded sectional view of the object of FIG. 8A along direction A—A.

Referring to FIGS. 8A and 8B, medial anchor strip 80 is designed for use with an elastomeric strap (not shown) which does not have a pile fabric layer attached. It is identical in configuration and function to the anchor strip 2 except that third layer 29 of strip 2 (FIG. 3) with its multiple hooked protrusions, is replaced by one or more buttons 81 attached to second layer 84. Buttons 81 engage button holes (not shown) disposed in the fabric of the elastomeric strap (not shown).

Figure 9A:
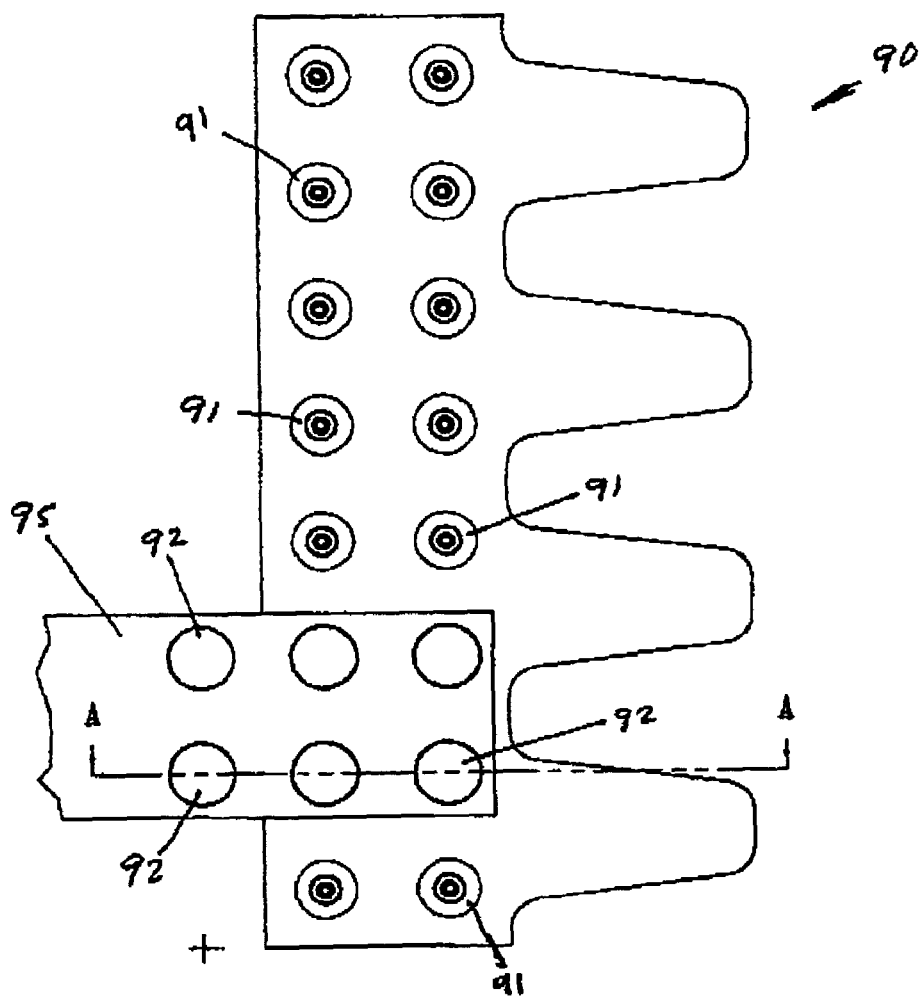
FIG. 9A is a plan view of an anchor strip and elastomeric strap having alternate fasteners (i.e., snaps).
Figure 9B:
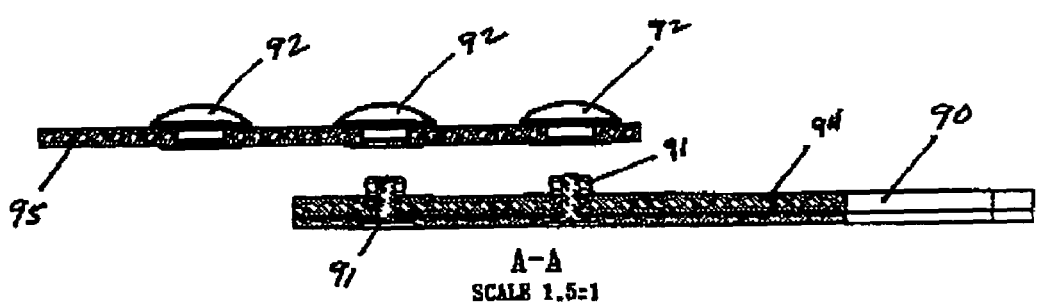
FIG. 9B is an expanded sectional view of the objects of FIG. 9A along direction A—A.

Referring to FIGS. 9A and 9B, medial anchor strip 90 is also designed for use with an elastomeric strap 95 which does not have a pile fabric layer attached. It is identical in configuration and function to the anchor strip 2 except that third layer 29 of strip 2 (FIG. 3) with its multiple hooked protrusions, is replaced by one or more snaps 91 attached to second layer 94. Snaps 91 engage mating snaps 92 disposed in the fabric of the elastomeric strap 95.

Patient comfort may be maximized by detaching either the medial or lateral end of a elastomeric strip from its respective anchor strip and increasing or decreasing the preload reducing force. Also, the elastomeric straps may be detached and the medial or lateral end of the strap moved vertically so as to add a vertical component to the reducing force. By trying various combinations of reducing force and reducing force direction, patient comfort can be maximized.

To do required chest expansion using the incentive spirometer, the preload in elastomeric straps 10, 11 and 12 is released by detaching one end of each strap from an anchor strip. After completion of the expansion, the elastomeric straps are reapplied in the manner described previously.

To shower, the patient removes the entire splint including the anchor strips. After showering the splint is reapplied by the patient in the manner described previously.

Figure 10:
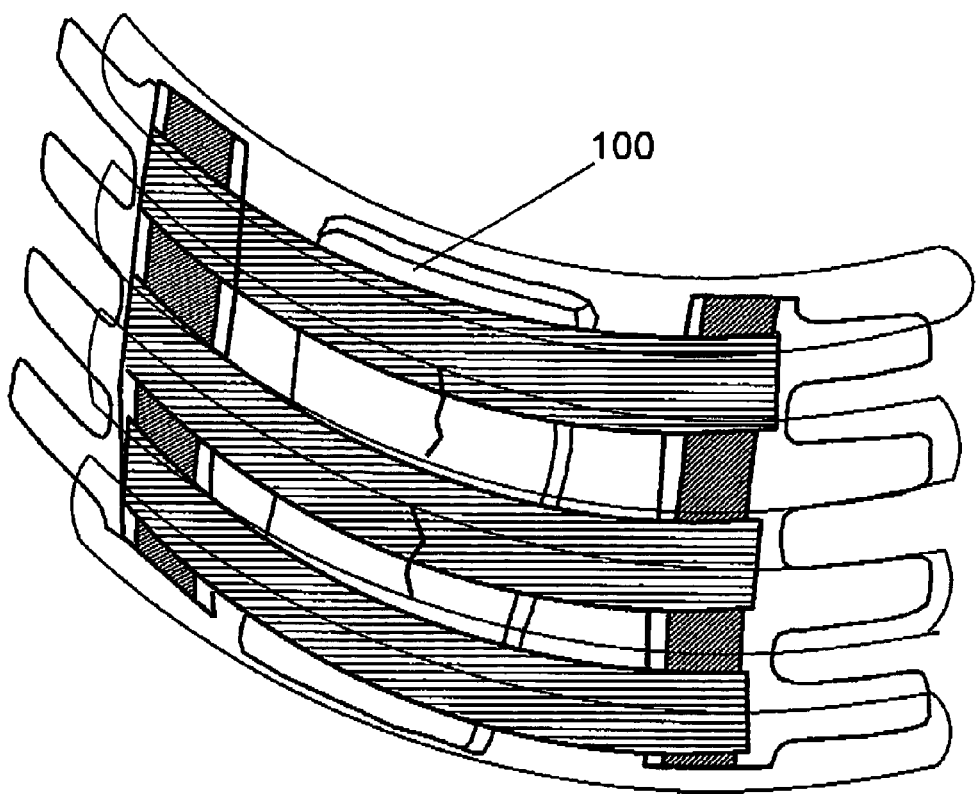
FIG. 10 is a perspective view of a rib splint constructed in accordance with the principles of the invention, in use and including a pad placed between the elastomeric strap(s) and the chest wall of the patient.

In an alternate embodiment a pad 100 is placed between the elastomeric straps and the chest wall so as to produce a stabilizing force component normal to the chest wall for added patient comfort. See FIG. 10.

Figure 11:
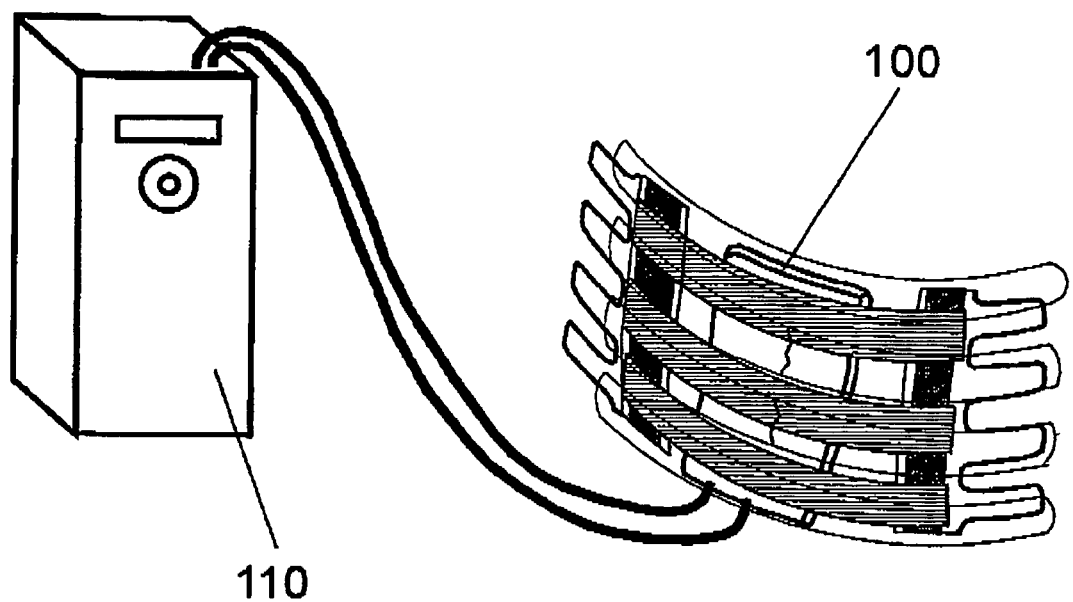
FIG. 11 is a perspective view of a rib splint constructed in accordance with the principles of the invention, in use and including a pad placed between the elastomeric strap(s) and the chest wall of the patient, further depicting the pad connected to a cold therapy machine.

In another embodiment the pad of the previous embodiment is a heated or cooled compress for enhanced pain relief, and in yet another embodiment the pad may be attached to a cold therapy machine 110 for additional pain relief. See FIG. 11.

The described embodiments are to provide illustration of the principles of the invention only. Those skilled in the art will recognize that variations and modifications may be made to the embodiments without changing the principles of the invention herein disclosed.

What is claimed is:

1. A method for splinting a rib injury comprising the steps of:
   a) attaching a pair of anchor strips which have a plurality of fasteners attached to one side of said strips, more or less vertically, to the surface of the skin of a chest cavity with an adhesive, said strips being more or less equidistantly displaced from a rib injury, in a manner to allow at least one elastomeric strap with at lest two fastener receivers to be positioned across the injury and said fastener receiver to be coupled to said fasteners;
   b) positioning at least one elastomeric strap with said fastener receivers across the injury, and stretching said at least one strap so as to produce an initial tension in said at least one elastomeric strap, and
   c) coupling said fasteners to said at least two fastener receivers which are attached to said at least one elastomeric strap, thereby providing a stabilizing force to said injury.

2. The method of claim 1 wherein said fasteners comprise a plurality of hooked protrusions.

3. The method of claim 2 wherein said fastener receivers comprise pile pads.

4. The method of claim 1 wherein said fasteners comprise buttons and said fastener receivers comprise button holes.

5. The method of claim 1 wherein the fasteners and fastener receivers comprise snaps.

6. The method of claim 1 further comprising the step of placing a pad between said at least one elastomeric strap and the chest wall.

7. The method of claim 6 wherein said pad is a heated compress.

8. The method of claim 6 wherein said pad is a cooled compress.

9. The method of claim 6 wherein said pad is connected to a cold therapy machine.

10. The method of claim 1 wherein said anchor strips comprise a plurality of elongated, laterally and medially extending portions.

11. The method of claim 6 wherein said anchor strips comprise a plurality of elongated, laterally and medially extending portions.

12. The method of claim 1, further comprising the step of periodically adjusting the tension of said at least one elastomeric strap to maintain sufficient tension to provide patient comfort.

13. The method of claim 1 wherein said fasteners comprise a plurality of hook portions.

* * * * *

UNITED STATES PATENT AND TRADEMARK OFFICE
CERTIFICATE OF CORRECTION

PATENT NO. : 6,971,995 B2
APPLICATION NO. : 10/764794
DATED : December 6, 2005
INVENTOR(S) : Michael A. Rolnick et al.

It is certified that error appears in the above-identified patent and that said Letters Patent is hereby corrected as shown below:

Column 4, line 41, please change "wit" to -- with --.

Column 4, line 43, please change "tat" to -- -that --.

Column 5, line 40, please change "lest" to -- least --.

Column 6, line 9, please insert the following phrase after the words "said injury":
--; and d) adjusting periodically the tension of said at least one elastomeric strap to maintain sufficient tension to provide patient comfort --.

Column 6, lines 35-40, please delete claims 12 and 13 in their entirety.

Signed and Sealed this

First Day of August, 2006

JON W. DUDAS
*Director of the United States Patent and Trademark Office*